United States Patent [19]
Theeuwes

[11] 3,977,404
[45] Aug. 31, 1976

[54] OSMOTIC DEVICE HAVING MICROPOROUS RESERVOIR

[75] Inventor: Felix Theeuwes, Los Altos, Calif.

[73] Assignee: Alza Corporation, Palo Alto, Calif.

[22] Filed: Sept. 8, 1975

[21] Appl. No.: 611,504

[52] U.S. Cl. .............................. 128/260; 128/130; 128/272; 128/271; 128/270; 222/389
[51] Int. Cl.$^2$ ........................................ A61M 31/00
[58] Field of Search ........... 128/260, 130, 269, 272, 128/127–129; 3/1; 424/19–21, 15, 37; 222/386.5, 389, 491; 206/.5

[56] References Cited
UNITED STATES PATENTS

| | | | |
|---|---|---|---|
| 3,765,414 | 10/1973 | Arlen | 128/260 |
| 3,845,770 | 11/1974 | Theeuwes | 128/260 |
| 3,851,648 | 12/1974 | Brooke | 128/260 |
| 3,878,977 | 4/1975 | Carlisle | 222/491 |

Primary Examiner—Aldrich F. Medbery
Attorney, Agent, or Firm—Paul L. Sabatine; Thomas E. Ciotti; Edward L. Mandell

[57] ABSTRACT

An osmotic device for delivering an active agent is disclosed. The device is comprised of a wall surrounding in at least a part, a reservoir containing agent. The wall is formed of a material permeable to an external fluid and impermeable to agent. The reservoir is formed of a microporous material permeable to agent and fluid, and having at least one micropore that is a passageway for release of agent. The agent is soluble in the fluid and exhibits an osmotic pressure gradient against the fluid, or the agent has limited solubility in the fluid and is admixed with an osmotically effective compound soluble in fluid that exhibits an osmotic pressure gradient against fluid. In operation, agent is released by fluid permeating through the wall into the reservoir producing a solution of agent or a solution of compound containing agent, which solution in either instance is released through the micropore to the exterior of the device.

38 Claims, 8 Drawing Figures

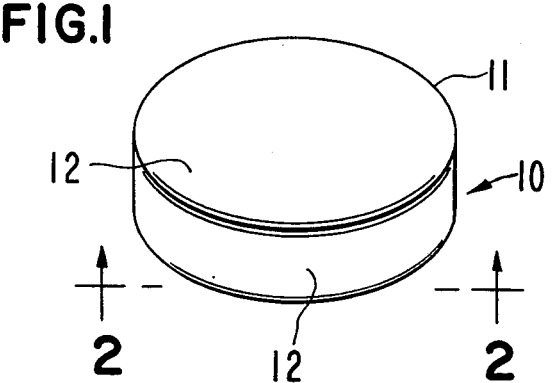
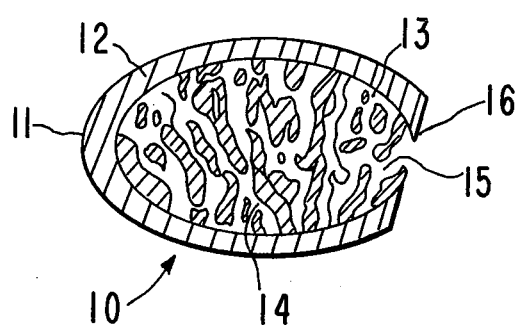
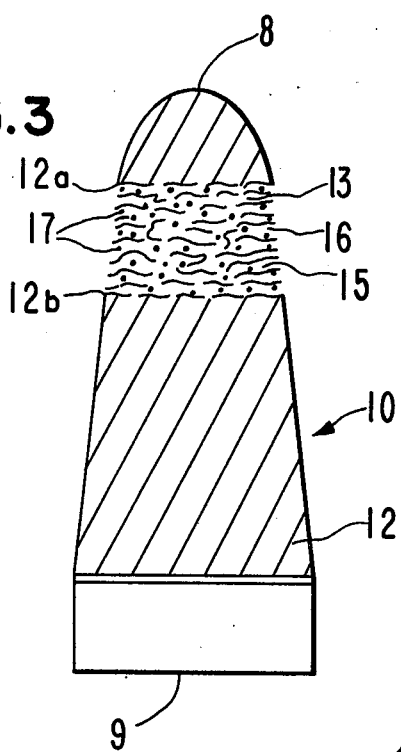
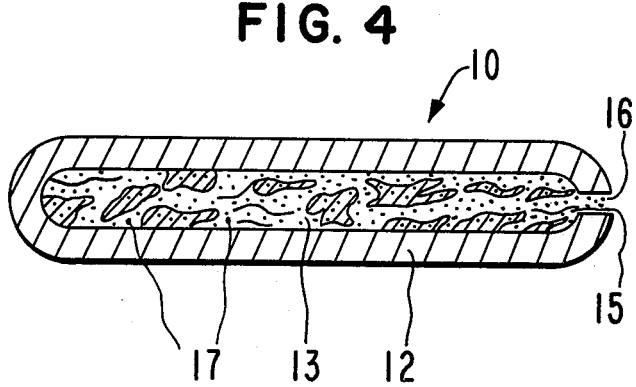
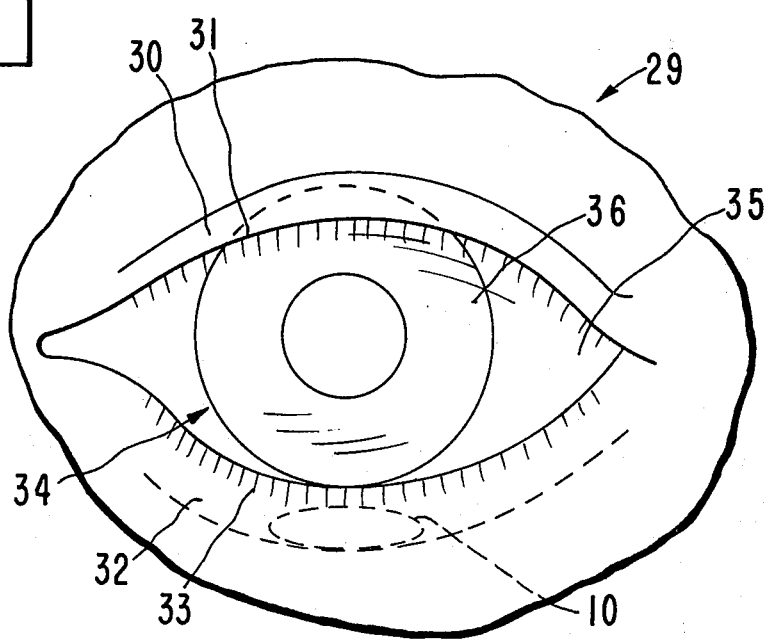

OSMOTIC DEVICE HAVING MICROPOROUS RESERVOIR

BACKGROUND OF THE INVENTION

1. Field of the Invention

This invention pertains to an osmotic device for delivering a useful agent at a controlled and continuous rate over a prolonged period of time to an environment of use.

2. Description of the Prior Art

Devices for the controlled and continuous delivery of an active agent made from microporous materials are known to the prior art. Generally, the agent is embedded in or surrounded by the material and its release therefrom often is adversely influenced by external conditions. For example, U.S. Pat. No. 2,846,057 discloses a device consisting of a porous cellophane wall surrounding sodium fluoride that is released by water flowing into the pores to dissolve and leach it from the device. Controlled release is hard to obtain with this device because release is governed by external conditions and not by the device. That is, the amount of fluoride released changes with the rate of flow of water, with higher rates increasing the amount released, and lower rates decreasing the amount released over time. Similarly, U.S. Pat. No. 3,538,214 discloses a device consisting of drug coated with a film of water-insoluble plastic containing a modifying agent that is soluble at a certain pH. When this device is in the gastrointestinal tract, the modifying agent is partially or fully dissolved from the film by gastrointestinal fluid to form a porous film. This lets fluid through the film to dissolve the drug and leach it outwards through the pores into the tract. Controlled release is difficult to achieve with this device because the selection of the modifying agent is based on the unknown acid and alkaline state of the gastrointestinal tract which concomitantly influences pore formation and the exposure of drug to fluid. A similar device is disclosed in U.S. Pat. No. 2,928,770. The device of this patent consists of an outer layer of drug coated onto a porous material having its pores filled with a softened wax that is supposedly removed in the gastrointestinal tract by the alimentary fluid. This device cannot be relied on for controlled release because it too requires in situ pore formation which is dominated by unregulated external conditions and not by the device.

Another device designed for the release of drug from an inert plastic matrix is described in *Acta Pharm. Suecica*, Vol. 8, pages 153 to 168, 1971, and in *J. Pharm. Sci.*, Vol. 60 pages 1028 to 1033, 1971. The device disclosed in these references consists of a porous poly(vinylchloride) matrix having drug embedded therein. Several disadvantages are associated with this device that tend to diminish its use as a reliable and dependable device. For example, the rate of release is stirring-rate dependent, as fluid must be in a constant flux to leach drug from the matrix. That is, a slight change in the direction and velocity of fluid can create a turbulence that unpredictably alters the movement of fluid into the pores, and the amount of drug released. Another disadvantage that occurs as drug leaves the device is the length of the diffusional path increases and the surface area of drug decreases. Both events cause the release rate from the matrix to decrease as a function of time. The release rate from the matrix also is pH dependent when a drug is contained therein that has a solubility that is dependent on pH. For these drugs, the amount of drug available for absorption varies with the location of the device in the gastrointestinal tract. A similar device is set forth in U.S. Pat. No. 2,987,445.

OBJECTS OF THE INVENTION

Accordingly, it is an immediate object of this invention to provide a novel device for delivering an active agent to produce a beneficial effect, which device overcomes the aforesaid disadvantages associated with the prior art devices.

Still another object of the invention is to provide a device for delivering an active agent at a controlled and continuous rate over a prolonged period of time, which delivery is controlled by the device and not by the environment of use.

Still a further object of the invention is to provide a device that can administer a complete dosage regimen for a prolonged time period, the use of which requires intervention only for initiation and sometimes for termination of the regimen.

Yet another object of the invention is to provide a device for the administration of a locally actng or systemically acting drug to produce a physiologic or pharmacologic effect in a host, and which device can administer the drug at a rate that does not vary with time.

Still another object of the invention is to provide a device that is simple in construction, designed with a minimum number of parts, is easy to use, and can contain high concentrations of active agent that is released substantially free of any stirring rate or pH dependency for the device.

Yet still another object of the invention is to provide an osmotic device for delivering an active agent over a range of release rates from very low to very high as controlled by the device, and which device maintains its physical and chemical integrity throughout the release period.

Yet still another object of the invention is to provide an erodible or biodegradable osmotic device that erodes or biodegrades after the device completes its release of active agent.

Other objects, features and advantages of the invention will be aparent to those skiled in the art from the following detailed description of this specification, taken in conjunction with the drawings and the accompanying claims.

SUMMARY OF THE INVENTION

This invention concerns an osmotic device comprised of a wall surrounding at least a part of a reservoir containing a useful agent and having a passageway for releasing agent from the device. The wall is comprised in at least a part of a material permeable to an external fluid present in the environment of use and substantially impermeable to agent. The reservoir is formed of a microporous material having voids and pores with the material permeable to agent and fluid and having agent dispersed in the material, the voids and pores. Or, the material is substantially impermeable to agent and the agent is dispersed in the voids and pores. Agent is released from the device through the passageway which consists of one or more micropores that communicate with the reservoir and the exterior of the device. Agent is released from the device by external fluid being imbibed through the wall into the reservoir in a tendency towards osmotic equilibrium at a rate determined by the permeability of the wall and the osmotic pressure gradient across the wall to continuously dissolve agent or a mixture of an osmotically effective compound and agent producing a substantially saturated solution of agent or of the compound containing agent, which solution in either instance is delivered through the passageway from the device. The device delivers agent at a controlled and continuous rate over a prolonged period of time because the rate of dissolution of agent is larger than the rate of release of agent from the device.

BRIEF DESCRIPTION OF THE DRAWINGS

In the drawings, which are not drawn to scale, but are set forth to illustrate various embodiments of the invention, the figures are as follows:

FIG. 1 is a view of an osmotic device of the invention designed for oral delivery of an active agent.

FIG. 2 is a cross-sectional view of the device of FIG. 1 taken through 2—2 with the walls removed for depicting the reservoir of the device.

FIG. 3 is another embodiment of the invention showing a side view of an osmotic device having a section of its wall removed with the device designed for delivering an agent in the anal canal.

FIG. 4 is an enlarged cross-sectional view of a similar embodiment depicting an ocular device consisting of a wall and a reservoir for housing agent.

FIG. 5 is a partly diagrammatic front elevational view of a human eye illustrating an ocular device in ophthalmic drug delivery operative position after insertion in the eye.

In the drawings and specifications, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 6:
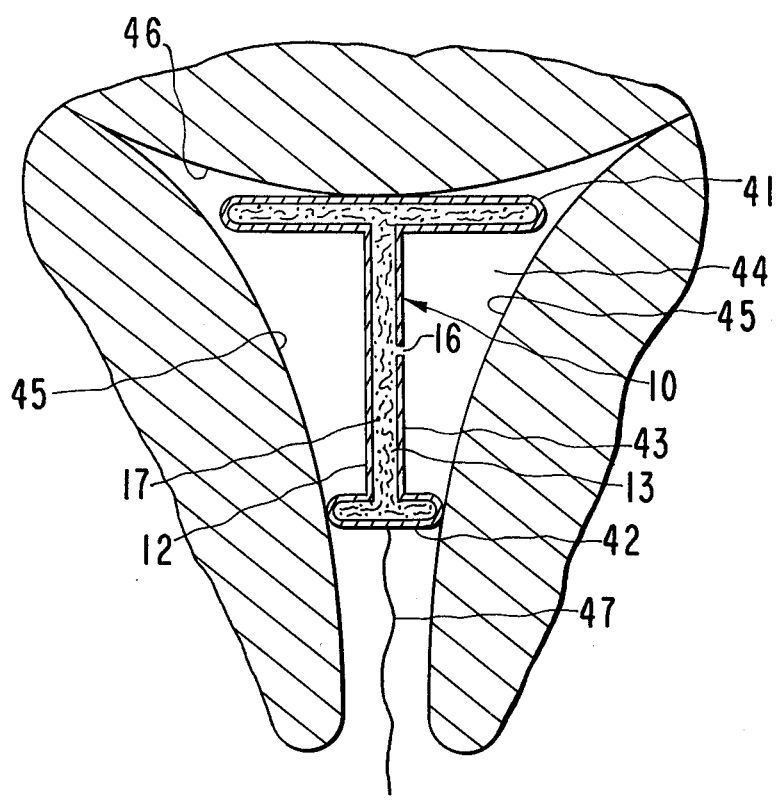
FIG. 6 is a fragmentary view of a uterine cavity showing an osmotic intrauterine device positioned in the uterine cavity.

Turning now to the drawings in detail, which are examples of devices of the invention, and which examples are not to be construed as limiting, one embodiment of a device is indicated in FIG. 1 by numeral 10. Device 10 is comprised of a body 11 consisting of a wall(s) 12 that surround a reservoir (not shown) that communicates through an opening (not shown) with the exterior of device 10.

Referring to FIG. 2, device 10 is seen in cross-section along line 2—2 of FIG. 1. As seen in FIG. 2, device 10 is comprised of a body portion 11 having a wall 12 surrounding a reservoir 13 formed of a microporous material having a passageway 15 that communicates with reservoir 13 and the exterior of device 10 through opening 16 in wall 12. Wall 12 surrounds, in at least a part, reservoir 13 and it is optionally coated or sprayed onto reservoir 13. Wall 12 is formed of a substantially imperforate, homogenous semipermeable material that is permeable to an external fluid and substantially impermeable to an active agent, not shown, that is housed in reservoir 13. Wall 12 is formed of a synthetic or naturally occurring semipermeable material, and a detailed description of these materials appears later in the specification.

Reservoir 13 is formed of a material having micropores 14 that are interconnected or form continuous paths with at least one of the micropores 14 functioning as a passageway 15 for the osmotic release of agent through opening 16 in wall 12 from device 10. That is, in a preferred embodiment of this invention, agent is released through a micropore that acts as an osmotic passageway connecting reservoir 13 to the exterior of device 10. The use of micropore 15 as a passageway for releasing agent eliminates a manufacturing step of forming a passageway in device 10. A single micropore 15 or a multiplicity of micropores 15 can be used as a passageway for release of agent with the proviso that when more than one micropore is used, release of active agent is by osmotic action and not by diffusion from the device. Reservoir 13 is formed of a naturally occurring or synthetically prepared solid or semi-solid microporous material that is compatible with external fluid that enters reservoir 13. The use of rapidly dissolving material, or of materials highly soluble in external fluids is to be avoided since dissolution of the reservoir will affect the constancy of agent release as well as the ability of the device to remain in place for prolonged periods of time. That is, reservoir 13 maintains its structural integrity as the microporous material forming reservoir 13 remains in device 10 throughout device 10's delivery period. Reservoir 13 houses an active agent, not shown, that is soluble in external fluid that enters the reservoir, or it houses a mixture of an osmotically effective compound soluble in external fluid that enters the reservoir and an active agent having limited solubility in the fluid. In an additional embodiment, reservoir 13 also provides support for forming device 10 with thin semipermeable membranes 12. This permits delivery of agent 17 from device 10 at substantially high rates. It also permits delivery of an agent having a low osmotic pressure, or of a mxiture of an agent mixed with other ingredients that have low osmotic pressure from device 10. A detailed description of microporous materials appears later in the specification.

Device 10 releases agent by supplying a saturated solution of dissolved agent or a saturated solution of dissolved osmotically effective compound containing agent to micropores 14 for it to flow in reservoir 13 ultimately reaching micropore 15 which terminates in opening 16 of wall 12. As agent leaves device 10, undissolved agent or undissolved osmotically effective compound in reservoir 13 dissolves in external fluid being imbibed through wall 12 to continuously form a saturated solution of agent, or a saturated solution of osmotically effective compound containing agent, which solution in either instance is released through micropore 15 at opening 16 to the exterior of device 10.

Device 10 of FIGS. 1 and 2 can be sized, shaped and adapted for releasing agent in many environments of use. Device 10 can be used for administering drug to humans, farm, domestic, sport and zoo animals, avians, fishes and reptiles. Device 10 can contain a high concentration of agent substantially free of having it leached from the device. The concentration, in a preferred embodiment, can be a complete pharmaceutical dosage regimen so that use of device 10 requires intervention only for initiation and sometimes for termination of the regimen. For example, device 10 can be designed for administering the regimen in the gastrointestinal tract at a rate controlled by the device substantially free of the pH of the tract and fluid movement in the tract, which administration requires intervention solely for swallowing the device.

FIG. 3 illustrates another device 10 designed for administering drug within a body opening, the anal canal (not shown). Device 10 is shaped like an obelisk having a lead end 8, a rear end 9 and it is comprised of a wall 12, with a section removed at 12a to 12b, surrounding a reservoir 13 for containing a drug 17. Wall 12 is formed of a semipermeable material having the properties described in FIGS. 1 and 2. Reservoir 13 is formed of a microporous mateial having a sponge-like appearance, seen in opened section 12A to 12b, with numerous interconnecting voids and pores 15. Drug 17 is dispersed throughout reservoir 13 and it is released from device 10 through a micropore 15 that leads to an aperture 16 in wall 12. Drug 17 is released by the osmotic mechanism described above.

FIGS. 4 and 5 illustrate another embodiment of the invention, an ocular device 10 for delivering drug to an eye 29. Referring first to FIG. 4, device 10 is seen in cross-section and it is comprised of a wall 12 surrounding a reservoir 13 containing a drug 17. Wall 12 is formed of a non-allergenic, biologically inert,, insoluble in tear fluid material that is permeable to eye fluid and substantially impermeable to drug 17. Reservoir 13 is formed of a microporous material having a plurality of micropores 15 containing drug 17 that is released from reservoir 13 to the exterior of device 10 through at least one micropore that ends at opening 16 in wall 12. The use of a microporous material for reservoir 14 has the additional advantage that very thin walls 12 can be used for device 10, and this also makes possible devices of high delivery rates. Drug 17 is present in reservoir 13 as a solid or semisolid, either alone or mixed with a carrier, and it is preferably in a form that does not leak from the device. It is preferred that wall 12 and reservoir 13 be made of semi-flexible or flexible materials for comfort in the user's eye.

Referring to FIG. 5, device 10 is seen in eye 29 for administering drug 17 to eye 29 at a metered dosage rate. In FIG. 5, eye 29 is comprised of an upper eyelid 30 with eyelashes 31 and a lower eyelid 32 with eyelashes 33. Eye 29 anatomically is comprised of eyeball 34 covered for the greater part by sclera 35 and at its center area by cornea 36. Eyelids 30 and 31 are lined with an epithelial membrane or palpebral conjunctiva, and sclera 35 is lined with a bulbar conjuctiva that covers the exposed surface of eyeball 34. Cornea 36 is covered with a transparent epithelial membrane. The portion of the palpebral conjunctiva which lines upper eyelid 30 and the underlying porton of the bulbar conjunctiva defines an upper cul-de-sac, while that portion of the palpebral conjunctiva which lines lower eyelid 32 and the underlying portion of the bulbar conjunctiva defines a lower cul-de-sac. Ocular device 10 is designed for placement in the upper sac or the lower sac. Device 10 is seen in broken continuous lines in the lower sac and it is held in place by the natural pressure of lower eyelid 32.

FIG. 6 depicts another embodiment of the invention shaped as an intrauterine device 10 comprised of two transverse members, a lead member 41 and a trailing member 42, connected through an elongated longitudinal member 43. Device 10 is sized and adapted for insertion and placement in uterine cavity 44 where it contacts sides 45 as well as fundus uteri 46 of uterus 44. A thread is attached to the trailing end 42 for manually removing device 10 from uterus 44. Device 10 is comprised of a wall formed of a semipermeable material surrounding a reservoir 13 made of a microporous material containing antifertility agent 17. An opening 16 in wall 12 serves as an exit aperture for releasing agent 17 from reservoir 13 into uterus 44. Agent 17 can be soluble in uterine fluid that enters reservoir 13 through wall 12 and exhibits an osmotic pressure gradient against the fluid, or agent 17 can have limited solubility in the fluid and have mixed therewtih an osmotically effective compound soluble in uterine fluid that exhibits an osmotic pressure gradient against fluid. Agent 17 also can be soluble in uterine fluid and in a form that is inactive until its release from device 10 where it is converted by uterus 44 to an active antifertility form.

While FIGS. 1 through 6 are illustrative of various devices that can be made according to the invention, it is understood these devices are not to be construed as limiting, as the devices can make a wide variety of shapes, sizes and forms for delivering agent to different environments of use. For example, the devices include buccal and vaginal devices, implants, pessaries, prosthestic devices, artificial glands, cervical devices and intrauterine devices of cylindrical, bullet, elliptical, circular, bulbous, loop, bow or any other shape that lends itself to uterine placement. Exemplary intrauterine devices include BirnBerg's Bow in U.S. Pat. No. 3,319,625, The Coment in U.S. Pat. No. 3,256,878, Majzlin Spring in U.S. Pat. No. 3,367,961, Inhiband in U.S. Pat. No. 3,323,520, Bakunin in U.S. Pat. No. 3,405,711, Shamrock in U.S. Pat. No. 3,077,879, and Ota's ring. The devices also include ocular devices of any geometric shape for comfortable placement in the cul-de-sac. Typical shapes include ellipsoid, bean, banana, circular, rectangular, doughnut, crescent and half-ring shaped devices. In cross-section the device can be doubly convex, concavo-convex, rectangular and the like, as the device in use will tend to conform to the shape of the eye. The dimensions of the ocular device can vary widely with the lower limit governed by the amount of drug to be supplied to the eye as well as by the smallest sized device that can be placed into the eye. The upper limit on the size of the device is governed by the space limitation in the eye consistent with comfortable retention in the eye. Satisfactory eye devices generally have a length of 4 to 20 millimeters, a width of 1 to 15 millimeters and a thickness of 0.1 to 4 millimeters. The ocular device can contain from 0.5 micrograms to 100 milligrams of drug, or more, and it can be made from non-erodile materials or materials that bioerode after the drug release period.

The devices made for oral use can have various conventional shapes and sizes such as round with a diameter of 3/16 inch to 1/2 inch, or it can be shaped like a capsule having a range of sizes from triple zero to zero, and from 1 to 8. The device also can be adapted for delivering an active agent in streams, aquariums, fields, factories, reservoirs, laboratory facilities, hot houses, transportation means, navel means, hospitals, veterinary clinics, nursing homes and other environments of use.

DETAILED DESCRIPTION OF THE INVENTION

In accordance with the practice of the invention, it has now been found the devices provide many advantages over previously used dissolution and diffusional operated devices. One advantage is the ease of construction of the device by standard manufacturing techniques into devices of various shapes, sizes and forms for delivering an agent to the environment of use. Another advantage of the device is it can be made with a minimum number of parts consisting of a wall and a reservoir for containing an active agent. Another advantage of the device is that release of agent is controlled by the device and not by the environment of use which release occurs substantially free of the external pH and may stirring rate dependency. Other advantages will become apparent to those versed in the art from the specification, the drawings and the accompanying claims.

Microporous materials suitable for making the reservoir of the devices of the invention can be described as having a sponge-like appearance that provides a supporting structure for microscopic-sized interconnected pores or voids. The materials can be isotropic wherein the structure is homogenous throughout a cross-sectional area, or they can be anisotropic wherein the structure is non-homogenous throughout a cross-sectional area. The pores can be continuous pores that have an opening on both faces of a microporous material, pores interconnected through tortuous paths of regular and irregular shapes including curved, curved-linear, randomly oriented continuous pores, hindered connected pores and other porous paths discernible by microscopic examination. Generally microporous materials are defined by the pore size, the number of pores, the tortuosity of the microporous path and the porosity which relates to the size and the number of pores. The pores size of a microporous material is easily ascertained by measuring the observed pore diameter at the surface of the material under the electron microscope. Generally, materials possessing from 5 to 95% pores and having a pore size of from 10 angstroms to 100 microns can be used for making the device. The pore size and other parameters characterizing the microporous structure also can be obtained from flow measurements, where a liquid flux, $J$, is produced by a pressure difference $\Delta P$, across a membrane. The liquid flux through a membrane with pores of uniform radium extended through the membrane and perpendicular to its surface is given by the relation 1:

$$J = \frac{N\pi r^4 \Delta P}{8\eta \Delta x} \qquad (1)$$

wherein $J$ is the volume transported per unit time and membrane area containing $N$ number of pores of radius $r$, $\eta$ is the viscosity of the liquid, and $\Delta P$ is the pressure difference across the membrane with thickness $\Delta x$. For this type of membrane, the number of pores $N$ can be calculated from relation 2, wherein $\epsilon$ is the porosity defined as the ratio of void volume to total volume of the membrane:

$$N = \left[ \frac{1}{\epsilon} \times \left( 1 - \frac{\text{weight of pourous membrane}}{\text{weight of membrane of same size but free of pores}} \right) \right] \qquad (2)$$

The pore radius then is calculated from relation 3:

$$r = \left( 8\eta \frac{J \cdot \Delta x \cdot \tau}{\Delta P \cdot \epsilon} \right)^{1/2} \qquad (3)$$

wherein $J$ is the volume flux through the membrane per unit area produced by the pressure difference $\Delta P$ across the membrane, $\eta$, $\epsilon$ and $\Delta x$ have the meaning defined above and $\tau$ is the tortuosity defined as the ratio of the diffusional path length in the membrane to the membrane thickness. Relations of the above type are discussed in *Transport Phenomena In Membranes*, by Lakshminatayanaiah, N, Chapter 6, 1969, published by Academic Press, Inc.

As discussed in this reference on page 336, in Table 6.13, the porosity of the membrane having pore radii $r$ can be expressed relative to the size of the transported molecule having a radius $a$, and as the ratio of molecular radius to pore size radius $a/r$ decreases, the membrane becomes porous with respect to this molecule. That is, when the ratio $a/r$ is less than 0.3, the membrane becomes substantially microporous as expressed by the osmotic reflection coefficient $\sigma$ which decreases below 0.5. Microporous materials with a reflection coefficient $\sigma$ in the range of from 0 to 0.5 and preferably less than 0.1 with respect to the active agent are suitable for fabricating the devices. The reflection coefficient is determined by shaping the material in the form of a membrane and carrying out water flux measurements as a function of hydrostatic pressure difference and as a function of the osmotic pressure difference caused by the active agent. The osmotic pressure difference creates an osmotic volume flux, the hydrostatic pressure difference creates a hydrostatic volume flux, and the reflection coefficient is expressed by relation 4:

$$\sigma = \frac{\text{hydrostatic pressure difference} \times \text{osmotic volume flux}}{\text{osmotic pressure difference} \times \text{hydrostatic volume flux}} \qquad (4)$$

Properties of microporous materials are described in *Science*, Vol. 170, pages 1302 to 1305, 1970; *Nature*, Vol. 214, page 285, 1967; *Polymer Engineering and Science*, Vol. 11, pages 284 to 288, 1971; U.S. Pat. Nos. 3,567,808 and 3,751,536; and in *Industrial Processing With Membranes*, by Lacey, R. E., and Loeb, Sidney, pages 131 to 134, 1972, published by Wiley, Interscience, New York.

Microporous materials are commercially available and they can be made by art known methods. The materials can be made by etched nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat.

Nos. 3,565,259; 3,615,024; 3,751,536; 3,801,692; 3,852,224; and 3,849,528.

Microporous materials useful for making the devices include microporous polycarbonates comprised of linear polyesters of carbonic acid in which carbonate groups recur in the polymer chain, microporous materials prepared by the phosgenation of a dihydroxyl aromatic such as bisphenol A, poly(vinylchloride), microporous polyamides such as polyhexamethylene adipamide, microporous modacrylic copolymers including those formed of poly(vinylchloride) 60% and acrylonitrite, styrene-acrylic and its copolymers, porous polysulfones characterized by diphenylene sulfone groups in a linear chain thereof, halogenated poly (vinylidene), polychloroethers, acetal polymers, polyesters prepared by esterification of a dicarboxylic acid or anhydride with an alkylene polyol, poly(alkylenesulfides), phenolic polyesters, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,061; 3,852,224; 3,853,601; and 3,852,388, in British Pat. No. 1,126,849, and in Chem. Abst., Vol. 71, 4274f, 22572f, 22573f, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, semi-solid cross-linked poly(vinylpyrrolidone), microporous materials prepared by diffusion of multivalant cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589, 3,541,005, 3,541,006, and 3,546,142, derivatives of poly(stryrene) such as poly(sodium styrenesulfonate) and poly(vinyl benzyltrimethylammonium chloride), the microporous materials disclosed in U.S. Pat. No. 3,615,024, and U.S. Pat. Nos. 3,646,178 and 3,852,224. Other microporous materials include those that slowly erode over time, or erode after the device has released the agent; such as, cross-linked gelatin, cross-linked poly(lactide), cross-linked poly(vinyl alcohol) and poly(glycolide).

The semipermeable materials useful for fabricating the wall of the devices are materials that do not adversely affect the agent, the environment of use, and can be used for making a multiplicity of devices for releasing a plurality of agents. The semipermeable materials are permeable to external fluid and substantially impermeable to agent. Semipermeable membranes suitable for the present purpose can be characterized by their ability to transport a solvent, such as water, which property can be expressed by the permeability coefficient $L_p$. The degree of semipermeability for a membrane with respect to a particular osmotically effective solute can be expressed by the reflection coefficient $\sigma$, with $L_p$ and $\sigma$ defined by relation 5:

$$J = \frac{A}{h} L_p (\Delta P - \sigma \Delta \pi) \tag{5}$$

wherein $J$ is the volume transported across the membrane per unit time, caused by an osmotic pressure difference $\Delta\pi$ and hydrostatic pressure difference $\Delta P$, $A$ is the membrane area, and $h$ is the membrane thickness. In relation 5 a reflection coefficient approximately equal to 1, indicates the membrane is ideally semipermeable, and a reflection coefficient approximately equal to zero, indicates the membrane is porous. The reflection coefficient $\sigma$ of a membrane can range from 1 down to 0 depending on the osmotically effective solute molecular size or species. That is, the reflection coefficient indicates the degree to which a membrane is semipermeable or porous. Generally, semipermeable membranes useful for the present purpose have a reflection coefficient from 0.5 to 1 with respect to the solute, and preferably larger than 0.8.

As seen from relation 5, the permeability coefficient $L_p$, can be measured by a conventional flow experiment using $\Delta P$ as driving pressure in the absence of solute $(\Delta \pi = 0)$, or it can be measured from an osmotic flow experiment driven by a solute with reflection coefficient of $(\sigma = 1)$ for the membrane, in absence of a hydrostatic pressure. The reflection coefficient can be measured from an osmotic flow experiment calculated from relation 6 where the symbols have the meaning stated above and the permeability coefficient $L_P$ is obtained as described above. Relation 6 is as follows:

$$\sigma = \frac{Jh}{AL_p \Delta \pi} \tag{5}$$

The osmotic pressure difference $\Delta\pi$ across the membrane can be measured by sampling both sides of the diffusion cell and measuring the osmotic pressure of each solution by vapor pressure osmometry.

Generally, membranes having a fluid permeability of $10^{-4}$ to 0.1 cc. mil/cm$^2$.hr. atmosphere, expressed per atmosphere of hydrostatic or osmotic pressure difference across the membrane at the temperature of use while simultaneously possessing a high degree of impermeability to the solute, are useful for manufacturing the devices. Also, among the suitable semipermeable membranes are film forming membranes that possess a water sorption greater than 1 percent and less than 50 percent by weight at ambient temperatures, with the presently preferred semipermeable membranes having a water sorption greater than 5 percent and less than 50 percent by weight at ambient temperatures.

The materials can be substantially insoluble in fluids or they can bioerode after a predetermined period of time with erosion taking place at the end of the agent release period. Exemplary semipermeable materials include commercially available cellulose acetate, cellulose triacetate, agar acetate, amylose triacetate, beta glucan acetate, beta glucan triacetate, acetaldehyde dimethyl acetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate chloroacetate, cellulose acetate ethyl oxalate, cellulose acetate methyl sulfonate, cellulose acetate butyl sulfonate, cellulose ethers, cellulose acetate propionate, poly(vinylmethyl ether) copolymers, cellulose acetate butyl sulfonate, cellulose ethers, cellulose acetate propionate, poly(vinylmethyl ether) copolymers, cellulose acetate diethylaminoacetate, cellulose acetate octate, cellulose acetate laurate, methyl cellulose, cellulose acetate p-toluene sulfonate, triacetate of locust gum bean, hydroxylated ethylene-vinyl acetate, cellulose acetate butyrate, perm-selective aromatic nitrogen containing polymeric membranes that exhibit water permeability and essentially no solute permeability, semipermeable membranes made from polymeric epoxides, materials made from copolymers of an alkylene oxide and alkyl glycidyl ether, semipermeable erodible polyglycolic or polylactic acid and derivatives thereof that erode after the device releases its agent, the selectively permeable materials of ionically associated polyelectrolytes, the selectively permeable polymers formed by the coprecipitation of polycation and a polyanion as described in U.S. Pat. Nos. 3,173,876; 3,276,586; 3,541,005; 3,541,006; 3,546,142; semipermeable materials prepared from polymeric systems according to the procedures described in U.S. Pat. Nos. 3,657,115 and 3,661,634, and in Ency. of Poly. Sci. and Tech., Vol. 3, pages 291 to 584, 1965, published by Interscience, New York, and ultrathin semipermeable membranes prepared according to the procedure in U.S. Pat. No. 3,580,841. Of course, other semipermeable materials operable for the purpose of the invention can be used within the spirit of the invention.

For a semipermeable material, the flux of an external fluid, that is, the rate of water vapor transmission through the material, is determined by using the procedure described in *Diffusion In Polymers*, by J. Crank and G. S. Park, pages 1 to 39, 1968, published by Academic Press, N.Y., and then expressing the results as WVTR, or water vapor transmission rate through a film in grams/100 in. $^2$/24 hr./1 mil thick film. Other WVTR values can be found in *Plastic Film Technology*, W. W. R. Park, 1969, published by Van Nostrand-Reinhold Inc., and in *Diffusion In Polymers*, pages 274 to 276. Typical values are set forth in Table 1, wherein the film is the material and WVTR is as defined.

TABLE 1

| Film | WVTR |
|---|---|
| Polyvinyl alcohol | 100 |
| Polyurethane | 30 – 150 |
| Methylcellulose | 70 |
| Cellulose acetate | 40 – 75 |
| Ethylcellulose | 75 |
| Cellulose acetate butyrate | 50 |
| Polyvinylchloride, cast | 10 – 20 |
| Polyvinylchloride, extruded | 6 – 15 |
| Polycarbonate | 8 |
| Polyvinylfluoride | 3 |
| Ethylene-vinyl acetate | 1 – 3 |
| Polyesters | 2 |
| Cellophane, polyethylene coated | >1.2 |
| Polyvinylidene fluoride | 1.0 |
| Polyethylene | 0.5 – 1.2 |
| Ethylene propylene copolymer | 0.8 |
| Polypropylene | 0.7 |
| Polyvinyl chloride, rigid | 0.7 |

The osmotically effective compounds that can be used for the purpose of the invention include organic and inorganic compounds that exhibit an osmotic pressure gradient against an external fluid across the semipermeable wall of the device. The compounds are preferably used mixed with an agent that has limited solubility in the external fluid that enters the device for forming a saturated solution of compound containing agent that is osmotically delivered from the device. The phrase "limited solubility" as used herein means the agent has a solubility of about less than 1% by weight in the external fluid in the reservoir. The compounds are used by homogenously or heterogenously mixing the compound or a mixture of compounds with an agent, either before they are charged into the reservoir or by self-mixing after they are charged into the reservoir. In operation, these compounds attract fluid into the device producing a solution of compound which is delivered from the device concomitantly transporting undissolved and dissolved agent to the exterior of the device. Osmotically effective compounds useful for the present purpose include magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phasphate, calcium lactate, d-mannitol, urea, inositol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37°C, in water, is listed in Table 2. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure difference is converted into osmotic pressure. In Table 2, osmotic pressure of from 20 ATM to 500 ATM are set forth; of course, the invention includes the use of lower osmotic pressure from zero and higher osmotic pressure than those set forth by way of example in Table 2. The osmometer used for the present measurements is identified as Model 302B, Vapor Pressure Osmometer, Hewlett Packard, Avondale, Penna.

TABLE 2

| Compound or Mixture | Osmotic Pressure (ATM) |
|---|---|
| Lactose - Fructose | 500 |
| Dextrose - Fructose | 450 |
| Sucrose - Fructose | 430 |
| Mannitol - Fructose | 415 |
| Sodium Chloride | 356 |
| Fructose | 355 |
| Lactose - Sucrose | 250 |
| Potassium Chloride | 245 |
| Lactose - Dextrose | 225 |
| Mannitol - Dextrose | 225 |
| Dextrose - Sucrose | 190 |
| Mannitol - Sucrose | 170 |
| Sucrose | 150 |
| Mannitol - Lactose | 130 |
| Dextrose | 82 |
| Potassium Sulfate | 39 |
| Mannitol | 38 |
| Sodium Phosphate Tribasic . 12H$_2$O | 36 |
| Sodium Phosphate Dibasic . 7H$_2$O | 31 |
| Sodium Phosphate Dibasic . 12H$_2$O | 31 |
| Sodium Phosphate Dibasic Anhydrous | 29 |
| Sodium Phosphate Monobasic . H$_2$O | 28 |

The expression "active agent" as used herein broadly includes any compound, composition of matter or mixture thereof, that can be delivered from the device to produce a beneficial and useful result. The agent can be soluble in a fluid that enters the reservoir and functions as an osmotically effective solute or it can have limited solubility in the fluid and be mixed with an osmotically effective compound soluble in fluid that is delivered from the device. The active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, micro-organism attenuators, and other agents that benefit the environment of use.

In the specification and the accompanying claims, the term "drug" includes any physiologically or pharmacologically active substance that produces a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes reptiles and zoo animals. The active drug that can be delivered includes inorganic and organic compounds without limitation, those materials that act on the central nervous system such as hypnotics and sedatives, including pentobarbital sodium, phenobarbital, secobarbital, thiopental and mixtures thereof, heterocyclic hypnotics such as dioxopiperidines and glutarimides, hypnotics and sedatives such as amides and ureas, exemplified by diethylisovaleramide and $\alpha$-bromoisovaleryl urea, hypnotic and sedative urethanes and disulfanes, pyschic energizers such as isocarboxazid, nialamide, phenelzine, imipramine, tranylcypromine and pargylene, tranquilizers such as chloropromazine, promazine, fluphenazine, reserpine, deserpidine, meprobamate, benzodiazepines such as chlordiazepoxide, anticonvulsants such as primidone, enitabas, diphenylhydantoin, ethltion, pheneturide and ethosuximide, muscle relaxants and antiparkinson agents such as mephenesin, methocarbomal, trihexylphenidyl, biperiden, levo-dopa also known as L-dopa and L-$\beta$-3-4-dihydroxyphenylalaine, analgesics such as morphone, codeine, meperidine, nalorphine, antipyretics and anti-inflammatory agents such as asprin, salicylamide and sodium salicylamide, local anesthetics such as procaine, lidocaine, naepaine, piperocaine, tetracaine and dibucane, antispasmodics and muscle contractants such as atropine, scopolamine, methscopolamine, oxyphenonium, papaverine, prostaglandins such as $PGE_1$, $PGE_2$, $PGF_2\alpha'$ $PGF_2\alpha$ and PGA, anti-microbials such as penicillin, tetracycline, oxytetracycline, chlorotetracycline, chloramphenicol and sulfonamides, anti-malarials such as 4-aminoquinolines, 8-aminoquinolines and pyrimethane, hormonal agents such as prednisolone, cortisone, cortisol and triamcinolone, androgenic steroids such as methyltestosterone, and fluoxmesterone, estrogenic steroids such as 17$\beta$-estradiol, $\alpha$-estradiol, estriol, $\alpha$-estradiol 3-benzoate, and 17-ethinyl estradiol-3-methyl ether, progestational steroids such as progesterone, 19-nor-preg-4-ene-3,20-dione, 17-hydroxy-19-nor-17-$\alpha$-preg-5(10-ene-3,20-yne-3-one, 17-ethinyl-17-hydroxy-5(10)-estren-3-one, and 9$\alpha$,10$\alpha$-pregna-4,6-diene-3,20-dione, sympathomimetic drugs such as epinephrine, amphetamine, ephedrine and norepinephrine, cardiovascular drugs such as procainamide, amyl nitrile, nitroglycerin, dipyredamole, sodium nitrate and mannitol nitrate, diuretics such as chlorathiazide, acetazolamide, methazolamide and flumethiazide, antiparasitics such as bephenium, hydroxynaphthoate, dichlorophen and dapsone, neoplastics such as mechlorethamine, uracil mustard, 5-fluorouracil, 6-thi-oguanine and procarbazine, hypoglycemic drugs such as insulin, isophane insulin, protamine zinc insulin suspension, globin zinc insulin, extended insulin zinc suspension, tolbutamide, acetohexamide, tolazamide and chlorpropamide, nutritional agents such as ascorbic acid, niacin, nicotinamide, folic acid, choline, biotin, pantothenic acid, and vitamin $B_{12}$, essential amino acids, essential fats, eye drugs such as pilocarpine, pilocarpine salts such as pilocarpine nitrate, pilocarpine hydrochloride, dichlorphenamide, atropine sulfate, scopolamine and eserine salicylate, and electrolytes such as calcium gluconate, calcium lactate, potassium chloride, potassium sulfate, sodium chloride, potassium fluoride, ferrous lactate, ferrous gluconate, ferrous sulfate, ferrous fumurate and sodium lactate. The beneficial drugs are known to the art in *Remington's Pharmaceutical Sciences*, 14th Ed., 1970, published by Mack Publishing Co., Easton, Penna.; and in *The Pharmacological Basis of Therapeutics*, by Goodman and Gilman, 4th Ed., 1970, published by The MacMillian Company, London.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent.

The amount of agent present in the device is initially in excess of the amount that can be dissolved in the fluid that enters the reservoir. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the device can house from 0.05 ng to 5 grams or more, with individual devices containing for example, 1 mg, 5 mg, 250 mg, 500 mg, 1.5 g, and the like.

The devices of the invention are manufactured by standard techniques. For example, one suitable method for making the microporous reservoir is to blend a polymeric powder with an agent in crystalline or granular form, and then applying pressure with or without heat to convert the blend into a solid having agent embedded therein. The solid is shaved, sized and adapted into the desired reservoir size. In operation, agent will be osmotically released forming a microporous reservoir with interconnecting voids, pores and channels. Another method for forming the reservoir consists in dispersing an agent in a liquid monomer and then polymerizing the monomer to yield a dispersion of agent in the polymer. This method can be varied by using mixtures of monomers and by adding polyfunctional monomers which can result in cross-linked systems. By means of this latter procedure, water soluble polymers and hydrophilic polymers can be used to make a reservoir. Then, the reservoir is sized and shaped according to the dimensions of the device. The reservoir also can be prepared from a microporous material previously formed from a polymer containing a soluble component that was leached therefrom, followed by soaking the microporous material in a saturated or supersaturated solution of agent to charge the reservoir with agent. The wall can be applied to the reservoir by spraying, dipping, casting, coating, solvent evaporation, molding or pressing the wall-forming material to the reservoir. The opening in the wall can be formed by covering a part of the wall with tape that is removed after the wall is coated onto the reservoir, by cutting away a part of the wall, or by punching an opening in the wall. The reservoir can also be formed by dispersing the agent, or a mixture of agent and an osmotic solute in a molten polymer to form a mixture that can then be injection molded or cast into a shaped reservoir. These are then coated with a semipermeable wall forming material. Also, the reservoir can be formed by mixing the agent into a polymeric solution that is subsequently cast and cured into a preselected shape. Other standard manufacturing procedures are described in *Modern Plastics Encyclopedia*, Vol. 46, pages 62 to 70, 1969; in *Remington's Pharmaceutical Science*, Fourteenth Edition, pages 1649 to 1968, 1970, published by Mack Publishing Company, Easton, Penna., and in *The Theory and Practice of Industrial Pharmacy*, by Lachman, et al, pages 197 to 225, 1970, published by Lea and Febiger, Philadelphia, Penna.

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic device for the controlled and continuous release of the drug potassium chloride, was manufactured as follows: first, a commercially available matrix consisting of microporous poly(vinylchloride) containing 750 mg of potassium chloride was coated with a semipermeable membrane consisting of cellulose acetate, E-320, commercially available from Eastman Kodak, by using the Wurster air suspension technique. A 5% polymer solution in acetone was used to apply coatings weighing 7.5, 16.5 and 24.5 mgs to three devices. These coatings correspond to thicknesses of 1, 2 and 3 mils, respectively. Next, the devices were dried for 1 week at 50°C to remove residual solvent. An aperture was made through the semipermeable wall of each device with a high speed drill to connect a microporous path of the reservoir with the exterior of the device.

Figure 7:
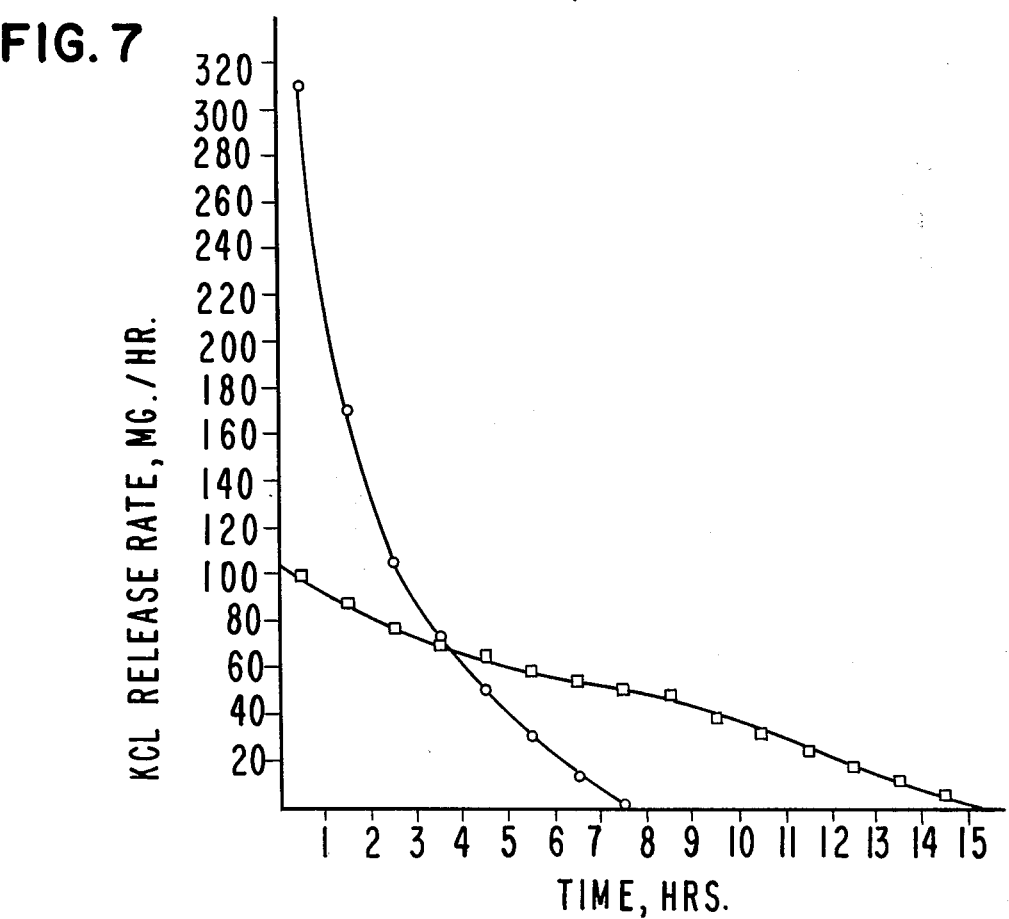
FIG. 7 is a graph comparing the release rate of a device consisting of an uncoated porous material with the release rate of a device consisting of a coated porous material.

The release rate for the devices was measured in a bath that consisted of a series of 15 test tubes with each tube containing 25 ml of distilled water at 77°C. The test was carried out by placing the devices in the first tube for 1 hour, then the device was transferred to the second tube for one hour, and then with matching places, into the remaining tubes. The devices were slowly oscilated throughout the test in the tubes containing the test solution. The amount of potassium chloride delivered was determined by electrical conductive measurements for each tube using a conductivity meter that was calibrated with known standards. The results of the tests are illustrated in FIG. 7. In FIG. 7, the curve through the circles is the release rate for an uncoated microporous poly(vinylchloride) reservoir containing 750 mg of potassium chloride and the curve through the squares indicate the release rate for microporous poly(vinylchloride) reservoir containing 750 mg of potassium chloride coated with 7.5 mg of semipermeable cellulose acetate.

EXAMPLE 2

An osmotic device was prepared as follows: first, a reservoir consisting of 750 mg of potassium chloride embedded in a porous poly(vinylchloride) matrix was dipped into a 10% w/w cellulose acetate solution in dioxane and the film-coated reservoir dried at 50°C for 24 hours. This produced a film having a thickness of about 5 mils. Next, an opening was formed in the film by removing 6 mm$^2$ of the film with a scalpel causing the micropores to be in communication with the reservoir and the exterior of the device. A second identical device was also prepared by this procedure.

Figure 8:
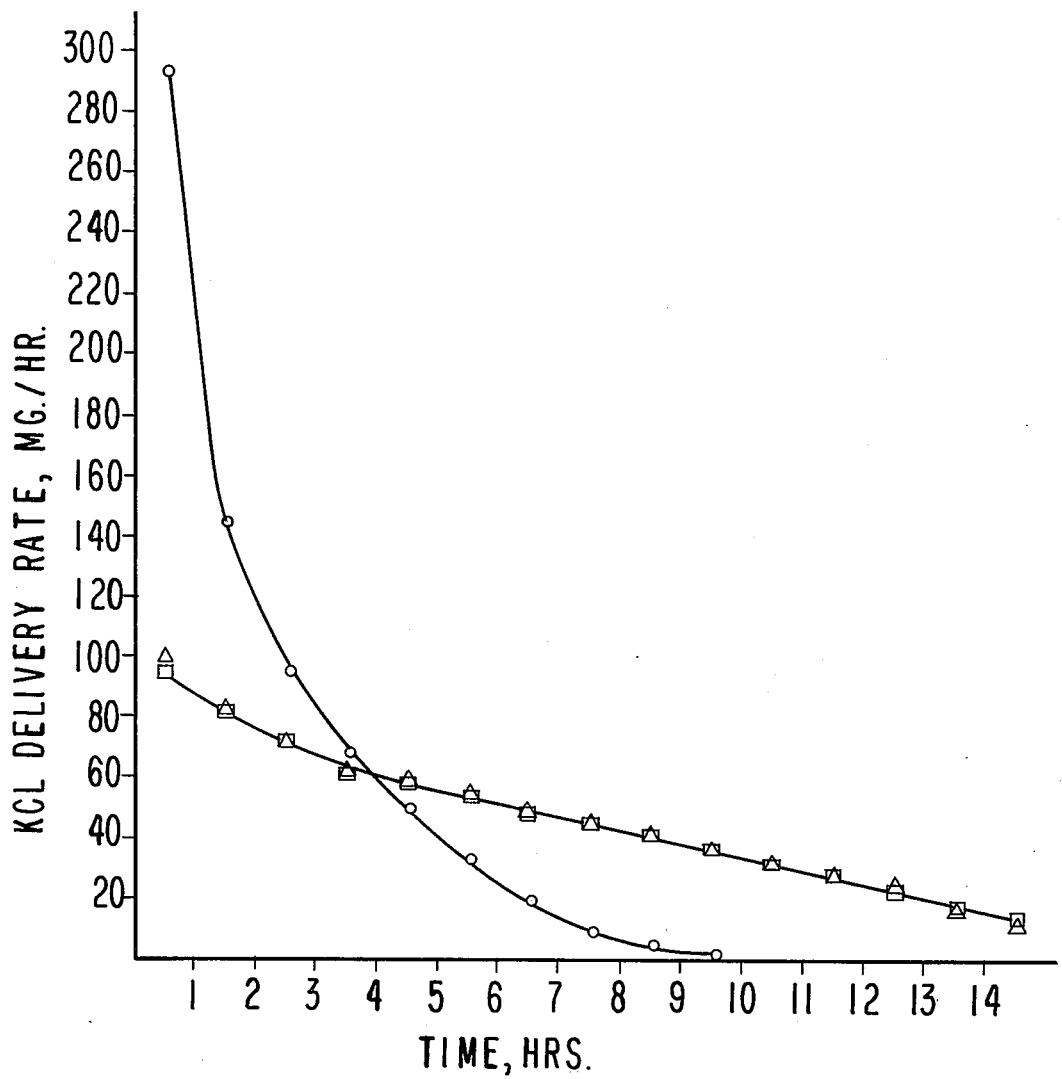
FIG. 8 is a graph comparing two similar devices each having a semipermeable wall surrounding a reservoir with a device consisting solely of an uncoated reservoir.

The devices were then placed in a bath which slowly oscillates the devices in test tubes containing 25 mil of distilled water at 37°C. After 1 hour, each device is automatically transferred to another test tube, and the one hour cycle repeated for a total of 15 hours or 15 tubes. A conductivity meter was used for measuring the amount of potassium chloride released after each hour. The release rate for an uncoated device also was measured by this procedure. The release rate for the devices is seen in FIG. 8. In the figure, the curved line plotted through the circles is the release rate for an uncoated device consisting of 750 mg of potassium chloride. The line plotted through the triangles and squares represents two devices having semipermeable walls with 6 mm$^2$ of their walls removed. The devices release potassium chloride over an extended 15 hour period, and simultaneously lower the first hour release rate peak by more than 60%. When the device is in an environment of use, for example, the gastrointestinal tract, the rate of release per unit time is substantially the same in gastric fluid as in intestinal fluid with release occuring independent of external factors such as enzyme concentration.

While the invention has been illustrated and described in detail, it is not intended to be limited to the details disclosed, since various modifications and changes may be made without departing in any way from the spirit of the present invention.

What is claimed is:

1. An osmotic device for the continuous dispensing of an active agent to an environment of use, said device comprising:
    a. a shaped wall formed of a semipermeable material that maintains its integrity during the dispensing period and is characterized as permeable to the passage of an external fluid in the environment of use and substantially impermeable to the passage of the active agent with the wall surrounding in at least a part;
    b. a reservoir formed of a material having a plurality of micropores with the reservoir containing an active agent that is soluble in the external fluid and exhibits an osmotic pressure gradient across the wall against the fluid;
    c. a passageway for dispensing agent from the device, said passageway consisting of at least one micropore that communicates with the reservoir and the exterior of the device; and d. wherein in operation with the device in the environment of use, external fluid is continuously imbibed through the wall into the reservoir in a tendency towards osmotic equilibrium at a rate determined by the permeability of the wall and the osmotic pressure gradient across the wall, thereby continuously dissolving the agent which is dispensed from the reservoir through the microporous passageway to the exterior of the device at a controlled rate over a prolonged period of time.

2. The osmotic device according to claim 1 wherein the reservoir is formed of a microporous material having a reflection coefficient of from 0 to 0.5.

3. The osmotic device according to claim 1 wherein the reservoir is formed of a microporous material consisting of from 5 to 95% pores having a pore size of 10 angstroms to 100 microns.

4. The osmotic device according to claim 1 wherein the reservoir is formed of a microporous material consisting of pores with a radius of $$r = \left( \pi \frac{J \cdot \Delta x \cdot J =}{\Delta P \cdot \epsilon} \right)^{1/2}$$

wherein $J$ is the volume flux, $\eta$ is the viscosity of the liquid, $\epsilon$ is the porosity, $\Delta P$ is the pressure difference across the material, $\Delta x$ is the thickness of the material and $\tau$ is the tortuosity.

5. The osmotic device according to claim 1 wherein the wall formed of a semipermeable material has a flux consisting of $$J = \frac{A}{h} L_p (\Delta P - \sigma \Delta \pi)$$

wherein $J$ is the volume of liquid transported across the wall, $A$ is the area of the wall, $h$ is the thickness of the wall, $L_P$ is the permeability coefficient, $\sigma$ is the reflection coefficient, $\Delta \pi$ is the osmotic pressure and $\Delta P$ is the hydrostatic pressure.

6. The osmotic device according to claim 1 wherein the active agent is a member selected from the group consisting of levo-dopa, aspirin, salicylamide, ferrous lactate, ferrous fumurate, ferrous gluconate, potassium sulfate, potassium chloride, potassium fluoride, chlorathiazide, acetazolamide, methazolamide, ascorbic acid, benzodiazepines, tolbutamide and chlorpropamide.

7. The osmotic device for the continuous dispensing of an active agent according to claim 1 wherein the reservoir is substantially insoluble in the external fluid and maintains its integrity during the dispensing period.

8. The osmotic device for the continuous dispensing of an active agent according to claim 1 wherein the agent is a member selected from the group consisting of locally and systemically acting drugs and the device is sized and adapted as a dosage form for the administration of agent to the gastrointestinal tract.

9. The osmotic device for the continuous dispensing of an active agent according to claim 1 wherein the agent is mixed with an inorganic or organic osmotically effective compound that exhibits an osmotic pressure gradient against the external fluid.

10. The osmotic device for the continuous dispensing of an active agent according to claim 9 wherein the osmotically effective compound exhibits an osmotic pressure of from 0 to 500 atmospheres.

11. The osmotic device for the continuous dispensing of an active agent according to claim 1 wherein the device is shaped and adapted for vaginal use.

12. The osmotic device for the continuous dispensing of an active agent according to claim 1 wherein the devices is shaped, sized and adapted for placement in the uterus.

13. The osmotic device for the continuous dispensing of an active agent according to claim 12 wherein the agent is a member selected from the group consisting of progestational and estrogenic steroids.

14. The osmotic device for the continuous dispensing of an active agent according to claim 1 wherein the device is structured and adapted to be placed in the anus.

15. The osmotic device for the continuous dispensing of an agent according to claim 1 wherein the semipermeable wall is formed of an erodible material.

16. The osmotic device for the continuous dispensing of an agent according to claim 1 wherein the reservoir is formed of an erodible material.

17. An osmotic device for continuously dispensing an active agent to an environment of use, said device comprising:

a. a shaped wall formed of a semipermeable material that is permeable to the passage of an external fluid and substantially impermeable to the passage of an active agent, said wall surrounding in part;

b. a compartment formed of a microporous material and having at least one micropore that communicates with the compartment and the exterior of the device, said compartment containing an active agent having limited solubility in the external fluid and an osmotically effective compound which exhibits an osmotic pressure gradient across the wall against the fluid;

c. a passageway for dispensing agent from the device, said passageway consisting of at least one micropore that communicates with the exterior of the device; and d. wherein in operation with the device in the environment of use, external fluid is imbibed through the wall into the compartment in a tendency towards osmotic equilibrium at a rate controlled by the permeability of the wall and the osmotic pressure gradient across the wall thereby continuously dissolving the compound, which as a mixture with the agent, is dispensed through the passageway at a controlled rate for a prolonged period of time.

18. The osmotic device for dispensing an active agent according to claim 17 wherein the agent is a drug.

19. The osmotic device for dispensing an active agent according to claim 17 wherein the osmotically effective compound exhibits an osmotic pressure of from 20 to 500 atmospheres.

20. The osmotic device for dispensing an active agent according to claim 17 wherein the active agent is a member selected from the group consisting of nutrient, vitamin and growth promoter.

21. The osmotic device for dispensing an active agent according to claim 17 wherein the agent is a member selected from the group consisting of biocide, insecticide, fungicide and algicide.

22. An osmotic device for the continuous dispensing of an active agent to an environment of use, said device comprising:

a. a shaped wall formed of a material that is permeable to the passage of an external fluid in the environment of use and substantially impermeable to the passage of an active agent with the wall surrounding;
b. a reservoir formed of a material having a plurality of micropores, said reservoir providing support for the wall and containing an active agent that is soluble in the external fluid and exhibits an osmotic pressure gradient across the wall against the fluid;
c. a passageway for dispensing agent from the device, said passageway consisting of at least one micropore that communicates with the reservoir and the exterior of the device; and,
d. wherein in operation with the device in the environment of use, external fluid is imbibed through the wall into the reservoir at a rate determined by the permeability of the wall and the osmotic pressure gradient across the wall, thereby dissolving the agent which is dispensed from the reservoir through the passageway to the exterior of the device at a controlled and continuous rate over time.

23. An ocular osmotic device for the continuous and prolonged administration of an ophthalmic drug, said device comprising:
a. an ophthalmic drug that exhibits an osmotic pressure gradient against eye fluid;
b. a shaped wall formed of a semipermeable material that maintains its integrity during the dispensing period and which material is permeable to the passage of eye fluid and substantially impermeable to the passage of drug, the wall surrounding in part;
c. a reservoir formed of a microporous material with the reservoir containing the drug;
d. a passageway for dispensing the drug from the device, said pasageway consisting of at least one micropore that communicates with the reservoir and the exterior of the device; and
e. wherein in operation with the device in the environment of use, eye fluid is continuously imbibed through the wall into the reservoir in a tendency towards osmotic equilibrium at a rate determined by the permeability of the wall and the osmotic pressure gradient across the wall, thereby dissolving the drug which is dispensed from the reservoir through the microporous passageway to the environment at a controlled rate over a prolonged period of time.

24. An ocular device for the dispensing of an ophthalmic drug according to claim 23 wherein the drug is a member selected from the group consisting of pilocarpine and its pharmaceutically acceptable salts.

25. An ocular device for the dispensing of an ophthalmic drug according to claim 23 wherein the ophthalmic drug is a member selected from the group consisting of epinephrine, ephedrine, norepinephrine, penicillin, tetracycline, oxytetracycline and chlorotetracycline.

26. An oral, osmotic device for the controlled and continuous dispensing of a unit dosage amount of drug to the gastrointestinal tract, said device comprising:
a. a shaped wall formed of a semipermeable material that is permeable to the passage of an external gastrointestinal fluid and is substantially impermeable to drug, said wall having an opening and surrounding;
b. a compartment formed of microporous material and containing a unit dosage amount of drug that is soluble in the fluid and exhibits an osmotic pressure gradient across the wall against the fluid when the device is in the environment of use;
c. a passageway for dispensing the drug, said passageway consisting of at least one micropore that communicates with the opening in the wall and the exterior of the device; and
d. wherein in operation with the device in the environment of use, external fluid is imbibed through the wall into the compartment in a tendency towards osmotic equilibrium at a rate controlled by the permeability of the wall and the osmotic pressure gradient across the wall producing a solution that is dispensed through the passageway from the device at a controlled and continuous rate over a prolonged period of time.

27. The oral device according to claim 26 wherein the drug is mixed with a member selected from the group consisting of inorganic and organic osmotically effective compounds that exhibit an osmotic pressure gradient across the wall against the fluid.

28. The oral device according to claim 26 wherein the drug is a member selected from the group consisting of acetazolamide, potassium chloride, ascorbic acid, acetylsalicyclic acid, levo-dopa, methazolamide, scopolamine, ferrous fumurate, ferrous lactate and nitroglycerin.

29. The oral device according to claim 26 wherein the wall is formed of a member selected from the group consisting of cellulose acetate, cellulose triacetate and cellulose acetate butyrate.

30. The oral device according to claim 26 wherein the microporous material maintains its integrity in the environment of use and has an osmotic reflection coefficient of from 0 to 0.5.

31. The oral device according to claim 30 wherein the reflection coefficient is the hydrostatic pressure difference times the osmotic volume flux divided by the osmotic pressure difference times the hydrostatic volume flux.

32. The oral device according to claim 26 wherein the compartment contains a member selected from the group consisting of a dispersant, emulsifier and wetting agent.

33. The oral device according to claim 26 wherein the wall is formed of an erodible material.

34. The oral device according to claim 26 wherein the compartment is formed of an erodible microporous material.

35. A method for continuously administering an active agent at a controlled rate to the gastrointestinal tract of a warm blooded animal comprising:
A. admitting into the gastrointestinal tract an osmotic device shaped and sized for oral administration with the device comprising;
  1. a wall formed of a pharmaceutically acceptable semipermeable material that is permeable to the passage of gastrointestinal fluid and substantially impermeable to the passage of an active agent, said wall having an opening and surrounding;
  2. a compartment formed of a microporous material and containing a unit dosage amount of active agent that is soluble in the fluid and exhibits an osmotic pressure gradient across the wall against the fluid;
  3. a passageway for dispensing the active agent, said passageway consisting of at least one micropore that communicates with the opening in the wall and the exterior of the device;

B. dissolving said agent in the compartment in gastrointestinal fluid being imbibed through the wall into the compartment at a rate determined by the permeability of the wall and the osmotic pressure gradient across the wall to continuously dissolve the agent; and C. releasing the agent from the device at a therapeutically effective controlled and continuous rate through the passageway to the gastrointestinal tract over a prolonged period of time.

36. A method according to claim 35 wherein the agent is a drug that produces a local or systemic effect on release from the device.

37. A method according to claim 35 wherein the agent is a powder and is mixed with an osmotically effective compound that exhibits an osmotic pressure gradient across the semipermeable wall against the fluid.

38. A method according to claim 35 wherein the microporous material is a solid.

* * * * *